US005661103A

United States Patent [19]

Harms et al.

[11] Patent Number: 5,661,103

[45] Date of Patent: *Aug. 26, 1997

[54] SEED TREATMENT COMPOSITION AND METHOD

[75] Inventors: David J. Harms, Naperville; Robert J. Ross, Elmhurst, both of Ill.; Alan M. Kinnersley, East Lansing, Mich.

[73] Assignee: Donlar Corporation, Bedford Park, Ill.

[*] Notice: The portion of the term of this patent subsequent to Sep. 27, 2014, has been disclaimed.

[21] Appl. No.: 447,784

[22] Filed: May 23, 1995

Related U.S. Application Data

[63] Continuation-in-part of Ser. No. 313,436, Sep. 27, 1994, Pat. No. 5,593,947, which is a continuation-in-part of Ser. No. 972,375, Nov. 5, 1992, Pat. No. 5,350,735.

[51] Int. Cl.$^6$ ..................................... A01N 37/44
[52] U.S. Cl. ............................. 504/147; 504/319
[58] Field of Search ..................... 504/319, 147

[56] References Cited

U.S. PATENT DOCUMENTS

| 4,172,072 | 10/1979 | Ashmead | 260/115 |
| 4,799,953 | 1/1989 | Danzig et al. | 71/98 |
| 4,813,997 | 3/1989 | Kinnersley et al. | 71/66 |
| 4,839,461 | 6/1989 | Bochmke | 528/363 |
| 4,863,506 | 9/1989 | Young | 71/113 |
| 4,863,898 | 9/1989 | Ashmead et al. | 514/6 |
| 5,059,241 | 10/1991 | Young | 71/106 |

OTHER PUBLICATIONS

Kinnersley et al., Plant Growth Regulation 9:137–146 (1990).
Byrnes, Fertilizer Research 26:209–215(1990).
Farm Chemicals Handbook, 1987, Meister Pub. Co., Willoughby, Ohio, p. B10.

*Primary Examiner*—S. Mark Clardy
*Assistant Examiner*—Brian G. Bembenick
*Attorney, Agent, or Firm*—Zarley, McKee, Thomte, Voorhees, & Sease

[57] ABSTRACT

Seedling development is enhanced by applying to the seeds, for example corn and soybeans, a water-soluble, nonaromatic polyamino acid such as polyaspartic acid. Time to germination is decreased, and rate of seedling development is increased. The composition may be applied to the seeds with a liquid or solid carrier or in combination with other seed treatments, such as nutrients and pesticides.

15 Claims, 2 Drawing Sheets

SEED TREATMENT COMPOSITION AND METHOD

CROSS REFERENCE TO A RELATED APPLICATION

This application is a continuation-in-part of Ser. No. 08/313,436 filed Sep. 27, 1994 and entitled "Method For More Efficient Uptake Of Plant Growth Nutrients" U.S. Pat. No. (5,593,947), which itself is a continuation-in-part of application Ser. No. 972,375, filed Nov. 5, 1992 and entitled "Composition And Method For Enhanced Fertilizer Uptake By Plants", now U.S. Pat. No. 5,350,735.

BACKGROUND OF THE INVENTION

Seed treatment compositions for agricultural crops are known. Many such treatments, however, are based upon compositions that have certain undesirable attributes, and in modern day farming might be termed as environmentally unsatisfactory. For example, treatment compositions that contribute to runoff causing environmental problems such as eutrophication of groundwater, nitrate pollution, phosphate pollution and the like are unsatisfactory. With the ever-increasing public concern for the environmental impact of materials placed in the soil, or at the point of treatment, there is an ever-increasing need for development of effective seed treatments which are environmentally satisfactory, which cause no harm to the plant, and which are effective for a broad spectrum of agricultural plants. This invention relates to such a seed treatment for decreasing germination time, increasing the rate of germination and increasing the percentage of seedling that develop.

This invention therefore has, as its primary objective, the fulfillment of the above needs, in particular, development of non-toxic and environmentally satisfactory seed treatment for crops such as corn, wheat, soybeans and other crops propagated from seed, that increases the rate of seed germination percent emergence as well as survivability of seedlings that emerge as plants.

An additional objective of the present invention is to provide a composition accomplishing each of the above enumerated objectives and/or advantages which contains a polyamino acid which is of a molecular weight sufficiently large that it will not be taken up by the seed or the emerging seedling, and at the same time will not cause environmental pollution during runoff.

Another objective of the present invention is to provide an environmentally acceptable non-toxic seed treatment which can be combined with other seed treatments or coatings such as insecticides and seed and seedling disease treatments and seed nutrients.

An even further objective of the present invention is to provide a composition which can be, at the user's option, used as a liquid seed treatment composition or in a dry composition for seed dusting.

Yet another objective of the present invention is to provide a seed treatment composition which can be used with monocotyledons such as corn and dicotyledons such as soybeans.

The method of accomplishing each of the above objectives of the invention as well as others will become apparent from the detailed description which follows hereinafter.

SUMMARY OF THE INVENTION

Seed treatment compositions of the present invention comprise environmentally acceptable non-toxic polyamino acids such as polyaspartic acid or salts thereof having a molecular weight larger than 1500. The composition may be applied to seeds in a suitable carrier such as water or a powder that is not harmful to the seeds or the environment. The seeds are then planted in conventional fashion. The mechanism of action which is not precisely known somehow allows the polyamino acid to enhance seedling development, that is, decreases the time for germination, increases the number of seeds that do germinate, and enhances seedling survivability. In addition, the composition may also be combined with nutrients and other seed treatments.

DETAILED DESCRIPTION OF THE INVENTION

Figure 1:
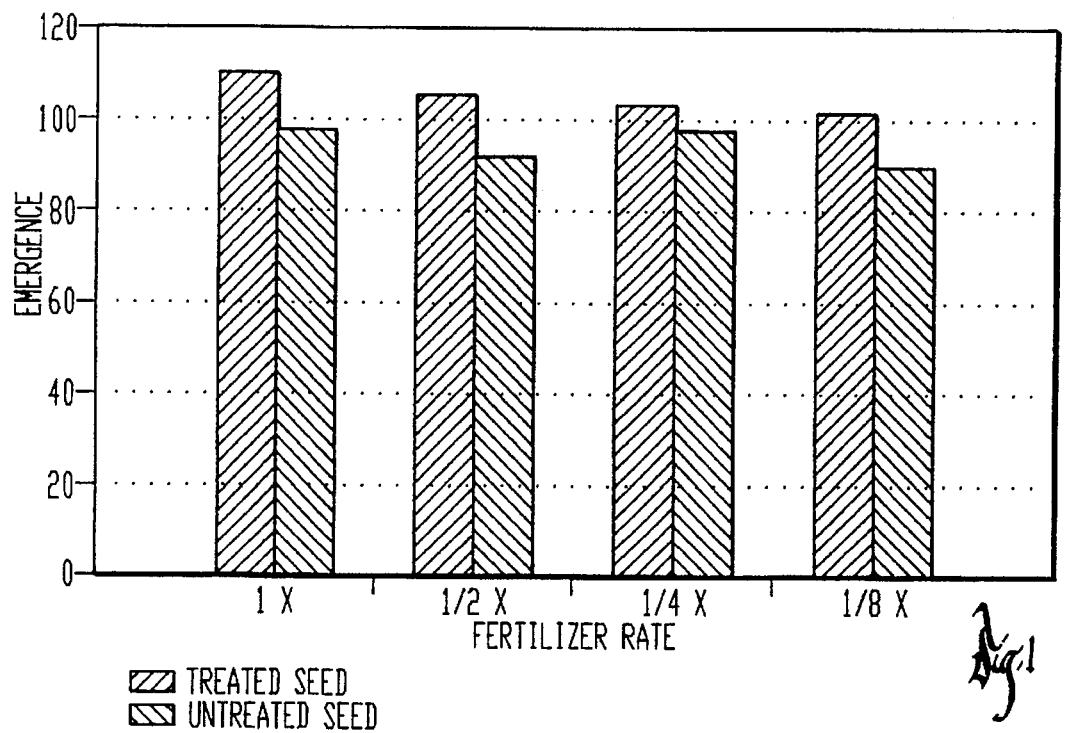
FIG. 1 shows Florida corn trials for the seed treatment of this invention of Table 1, graphically illustrated for trial 1 (Nov. 18, 1993).
Figure 2:
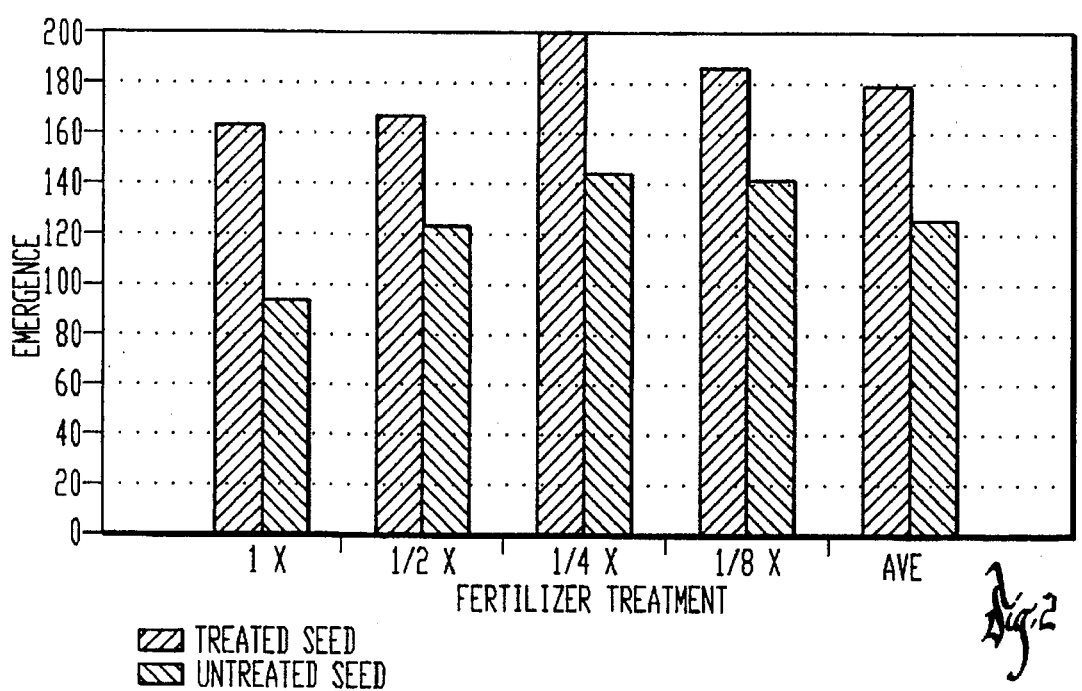
FIG. 2 shows Florida soybean trials for the seed treatment of this invention of Table 2, graphically illustrated for trial 5 (Nov. 04, 1993).

The present invention is premised upon the fact that it has been discovered that certain compounds, namely certain polymeric organic amino acids as set forth in our earlier co-pending application and issued U.S. Pat. 5,350,735 can be used in a seed treatment composition and applied directly but not limited to seeds such as corn, soybean and wheat with the result being that time to germination is decreased, the number of seeds that germinate is increased, and the survivability of the seedlings is enhanced. While not wishing to be bound by any theory, it is believed that polymeric organic acids may somehow interact with the soil and the nutrients in the soil to otherwise enhance the effect of those nutrients, as they interact with the seed.

In general, the polymeric organic acids can be applied directly to the seed as a solution or in combination with other commercially available additives. Solutions containing the polymeric organic acid can be sprayed or otherwise applied to the seed such as in a seed soak. Solids or dry materials containing the polymeric organic acid are also useful to promote effective seed growth. The solids or dry materials can be applied as a powder or dusting composition.

The polymeric organic acids, to be suitable for the practice of the present invention, must be water-soluble, non-aromatic, and must have a molecular weight sufficiently large to preclude absorption into the plant's own system. To that end, the non-aromatic polymeric organic acid units (residues), or mers, in the linear polymer chain that constitutes the polymeric acid. Polymeric organic acids having a molecular weight in excess of about 100,000 usually exhibit poor solubility in water for the present purposes, thus for present purposes a polymeric organic acid molecular weight not larger than about 100,000 is preferred. Particularly preferred molecular weight is in the range of about 1,500 to about 40,000.

Illustrative are polymeric organic acids, with or without carboxylic acid, thiocarboxylic acid, imidocarboxy, and/or amino side chains, such as, for example, polyacrylic acid, polymaleic acid, polylysine, polyglutamic acid, polyaspartic acid, polyglycine, polycysteine, polycysteine/glutamic acid, mixtures of the foregoing, and the like. Block or random copolymers or terpolymers of several organic acids are also within the purview of the present invention as the polymeric acid component thereof. For example, the utilized polymeric acid component can be a block copolymer of aspartic acid residues and L-lactic acid residues, a random copolymer of aspartic acid residues and glycolic acid residues, a conjugated protein constituted by amino acid residue chains interconnected by one or more polycarboxylic acid residues, a copolymer of acrylic acid and acrylamide, and the like.

Polymers of organic acids are commercially available. In addition, such polymeric acids, especially poly(amino acids), can be made, inter alia, by thermal condensation methods. See, for example, U.S. Pat. No. 5,057,597 to Koskan, Little et al., American Chemical Society 97:263–279 (1991), and U.S. Pat. No. 4,696,981 to Harada et al.

The starting materials for the polymerization, i.e., the organic acids, can exist as optical isomers, depending upon their respective structures, and can be polymerized either as a racemic mixture or as segregated optical isomers.

A racemic mixture is an equal molar mixture of the two possible optical isomers—the levorotatory and dextrorotatory isomers. Levorotatory (1) isomers are isomers of an optically active compound which rotate a beam of polarized light to the left; the dextrorotatory (d) isomers are isomers of the same compound which rotate a beam of polarized light to the right. Another convention employed to define the configurational relationships of dissimilar functional groups bonded to an asymmetric carbon atom, the so-called Fischer Method, is based on the geometric arrangement of functional groups relative to each other rather than on the direction (left or right) in which a standard solution of the compound rotates a beam of polarized light. The Fischer Method is well known in the art, and is discussed in more detail in Ficser & Ficser, *Introduction to Organic Chemistry*, D.C. Heath and Co., Boston, Mass., (1957) at pages 209–215. The Fischer Method designations are used herein.

In accordance with the Fischer Method, any compound which contains an asymmetric carbon atom of the same configuration as the asymmetric carbon in the arbitrary standard, dextrorotatory glyceraldehyde, is classified in the D series, while compounds in which the asymmetric carbon atom has the opposite configuration are classified in the L series. Although the Fischer D and L classifications do not correlate with dextro-(d) and levorotatory (1) optical activity for all compounds, those classifications can be used in combination with the optical activity classifications d and l define both the geometric arrangement and specific optical activity of any optically active isomer. Thus, the L-isomer of lactic acid, which is dextrorotatory, is defined as L-(d)-lactic acid, and the D isomer is defined as D-(1)-lactic acid. However, both of these characteristics of relatively simple compounds can be adequately defined by reference to only one classification system. For example, L-lactic acid is known to be dextrorotatory and l-lactic acid is known to have the D configuration according to Fischer. For this reason, the D and L isomers of lactic acid and other relatively simple organic acids are usually identified only by the D and L designations, and without explicit reference to their optical activity.

For organic acids that exhibit optical activity, the polymers and copolymers of the L-isomers are preferred. However, racemic mixtures as well as polymers and copolymers of the D-isomers can be utilized for the present purposes.

In some instances either the L-form or the D-form may exhibit greater biological activity vis-a-vis plant growth promotion. In such instances the more active form is, of course, the preferred form.

Particularly well suited for the practice of the present invention are the non-chelating polyorganic acids such as polyacrylic acid and the like, as well as the polyamino acids such as polyaspartic acid having a molecular weight in the range of about 1,500 to about 40,000, polyglutamic acid having a molecular weight in the range of about 4,000 to about 14,000, polyglycine having a molecular weight in the range of more than 1,500 to about 7,000, and polylysine having a molecular weight in the range of about 2,000 to about 7,000.

The term "chelate", as used herein in its various forms, refers to a complex formed by a polydentate ligand, i.e., a ligand that supplies more than one pair of electrons to a cation. See, for example, Masterson et al., *Chemical Principles*, 6th ed., Saunders College Publishing Co., Philadelphia, Pa. (1985), p. 635.

Similarly, the term "chelating agent", as used herein in its various forms, refers to a ligand that possesses at least two pairs of unshared electrons which pairs are far enough removed from one another to give a ring structure with a stable geometry, Ibid, p. 638.

The presently contemplated polyorganic acids are not chelating agents, and as such do not form chelates with the plant nutrients.

A preferred composition for the seed treatment of the present invention is polyaspartic acid as above mentioned. Polyaspartic acid may be used as the sole seed treatment, or it may be used in combination with other conventional seed treatments such as insecticides, seed nutrients, herbicidal antidotes, and seed and seedling disease treatments.

While it is preferred that the polyaspartic acid be used as the sole treating agent in a solubilizing carrier such as water, other treating agents can be used as well, such as seed nutrients, insecticides and seed and seedling disease treatments. In addition, small amounts of drying agent enhancers such as lower alcohols, etc. can be utilized in the composition. If desired, surfactants, emulsifiers and preservative may also be added at small (0.5% by weight or less) levels in order to enhance the stability of the seed coating product.

The seed coating composition may be a liquid carrier composition, as when the polyamino aspartic acid is solubilized in water, or it can be a powder composition with the conventional tackiness additives to assure that it will stick and coat the seeds. Suitable tacking talcs are graphites and cellulosic materials such as carboxymethyl cellulose and the like.

The seeds may be coated using a variety of methods including, but not limited to, pouring or pumping an aqueous solution of polyaspartate into a mixing device containing seeds, spraying an aqueous solution of polyaspartate into a mixing device containing seeds, spraying an aqueous solution of polyaspartate onto a layer of seeds on a conveyor system. The mixing devices useful in the present invention include, but are not limited to, tumblers, such as cement mixers and roller mills, and fluidized bed reactors. A stream of dry air may optionally be used to aid in the drying of the seed coatings. The drying can be performed simultaneous to the coating or after coating. The aqueous solution of polyaspartate may be an aqueous solution of polyaspartic acid or salts of polyaspartic acid. The salts of polyaspartic acid are preferably sodium, potassium or ammonium salts. The salt of polyaspartic acid is most preferably the sodium salt. The molecular weight of the polyaspartate may be from about 1500 to about 100,000. The molecular weight of the polyaspartate is preferably from about 1500 to about 40,000. The concentrations of the aqueous solution of polyaspartate useful in the present invention are preferably from about 10% by weight to about 60% by weight. The concentrations of the aqueous solution of polyaspartate useful in the present invention are most preferably from about 20% by weight to about 30% by weight.

The seed coatings were performed in the following fashion: Seed corn or seed soybeans (0.454 Kg) were placed in a 4 L volume metal cylinder on a roller mill. The lid of the metal cylinder had about a 5 cm diameter hole in the middle. The mill was tilted at about a 30 degree angle to keep any seeds from coming out of the hole in the lid. The mill was started with a rotation rate of about 60 rpm and 6.0 mL of 28% (w/w) aqueous solution of sodium polyaspartate was added in 1 mL increments over 20 minutes. An air hose was placed in the hole in the can lid and a stream of dry air was passed over the seeds, while still tumbling, for about 30 minutes. An additional 3 mL of 28% aqueous sodium polyaspartate was then added over about 10 minutes and the air stream was continued for an additional 30 to 40 minutes until the seeds were freely tumbling without sticking.

The seeds to which the treatment is applied can be either monocotyledons such as corn and wheat or dicotyledons such as soybeans. The seed coating may also be used for seeds of fruits and vegetables such as melons, tomatoes and lettuce.

The following examples all further illustrate but do not limit the process and compositions of the present invention.

EXAMPLE 1

Corn seeds were coated with a solution of 50% on a weight basis concentration of sodium polyaspartate and water. Seeds were mixed with the water solution of sodium polyaspartate which at this concentration was distinctly tacky. After thoroughly mixing, the seeds were allowed to air dry. In the tests shown below, conventional fertilizer, that is nitrogen, potassium and phosphorous, was used at the normal rate used by the farmer who participated in the test. The reference to "1X" means the farmer's normal fertilizer at the normal rate of application. ½X means one-half of the farmer's normal rate and ¼X means one-fourth of the farmer's normal rate, etc. Several tests were conducted over a two-year period to determine if sodium polyaspartate would in fact increase speed of germination, i.e. the amount of time it takes for the seedling to germinate, and as well, increase the stand (percent of emerging plants). In this example for corn located in Florida, corn was planted in conventional methods at different fertilizer levels as illustrated in Table 1. FIG. 1 graphically illustrates Table 1, (trial 1), with the X axis being the fertilizer application rate and the Y axis being the stand count or the number of plants in a given uniform plot.

Table 1 (below) shows the results of seed treated with sodium polyaspartate and untreated seed. FIG. 1 shows the results for trial number 1. It can be seen in Table 1 that the plot with seed treated with sodium polyaspartate had a higher stand count than those with untreated seed. The numbers are significant and indicate that assuming the plant progressed normally to maturity, there would be a substantially increased yield.

TABLE 1

CORN EMERGENCE FROM SEED
(No. of Plants per 80 feet of row)

| Date | Fertilizer Rates | | | |
|---|---|---|---|---|
| | 1× | ½× | ¼× | ⅛× |
| 10/18/93 | | | | |
| treated | 109.67 | 104.75 | 102.75 | 101.00 |
| control | 97.00 | 91.50 | 97.25 | 89.50 |
| 10/19/93 | | | | |
| treated | 110.67 | 105.00 | 107.00 | 107.00 |
| control | 100.67 | 97.75 | 99.50 | 92.75 |
| 10/20/93 | | | | |
| treated | 110.33 | 104.75 | 106.50 | 107.75 |
| control | 100.00 | 96.75 | 98.00 | 92.00 |

EXAMPLE 2

Soybean seed in Florida was divided into two parts. The seed was all taken from the same bag. One-half of the seed had sodium polyaspartate applied to it in the manner and the level of concentration set forth in Example 1, and the other one-half of the seed was used from the same bag in an untreated condition. Emergence was monitored beginning 5 days after planting with the treated seed averaging 35% more plants than the untreated seed. Seven days after planting there was an average of approximately 46% more plants in the treated seed plots than in the untreated seed plots (see Table 2 below). Thirty days after planting a reading was taken to determine the final stand. At this time the average number of plants in the plots where seed was treated was 42% greater than on those plots that did not receive the sodium polyaspartate treatment.

In this test, as in Example 1, the seed was coated with a solution of 50% by weight of sodium polyaspartate by simply adding water and then mixing the solution to the seed and then allowing it to self dry. Shelf life of treated seed was checked by saving part of the treated seed until the next spring and planting in the Midwest where substantially similar results were obtained, thus verifying the data.

TABLE 2

SOYBEAN EMERGENCE FROM SEED
(No. of Plants Per 80 Feet of Row)

| Trial Sets | Treatment | Fertilizer Rates | | | | Avg. Stand |
|---|---|---|---|---|---|---|
| | | 1× | ½× | ¼× | ⅛× | |
| 1st set | treated | 145.0 | 155.5 | 210.8 | 159.0 | 167.6 |
| | control | 89.0 | 119.3 | 138.5 | 146.5 | 123.4 |
| 2nd Set | treated | 158.7 | 182.8 | 213.8 | 201.0 | 189.0 |
| | control | 95.7 | 127.8 | 142.5 | 154.0 | 130.0 |
| 3rd Set | treated | 158.7 | 179.8 | 214.5 | 196.3 | 187.3 |
| | control | 97.7 | 130.8 | 146.8 | 148.7 | 131.0 |
| 4th Set | treated | 158.0 | 175.3 | 210.0 | 194.3 | 184.4 |
| | control | 96.7 | 127.8 | 145.8 | 146.7 | 129.2 |
| 5th Set | treated | 163.0 | 167.0 | 200.0 | 186.3 | 179.1 |
| | control | 93.7 | 123.5 | 144.3 | 142.0 | 125.9 |

EXAMPLE 3

Figure 3:
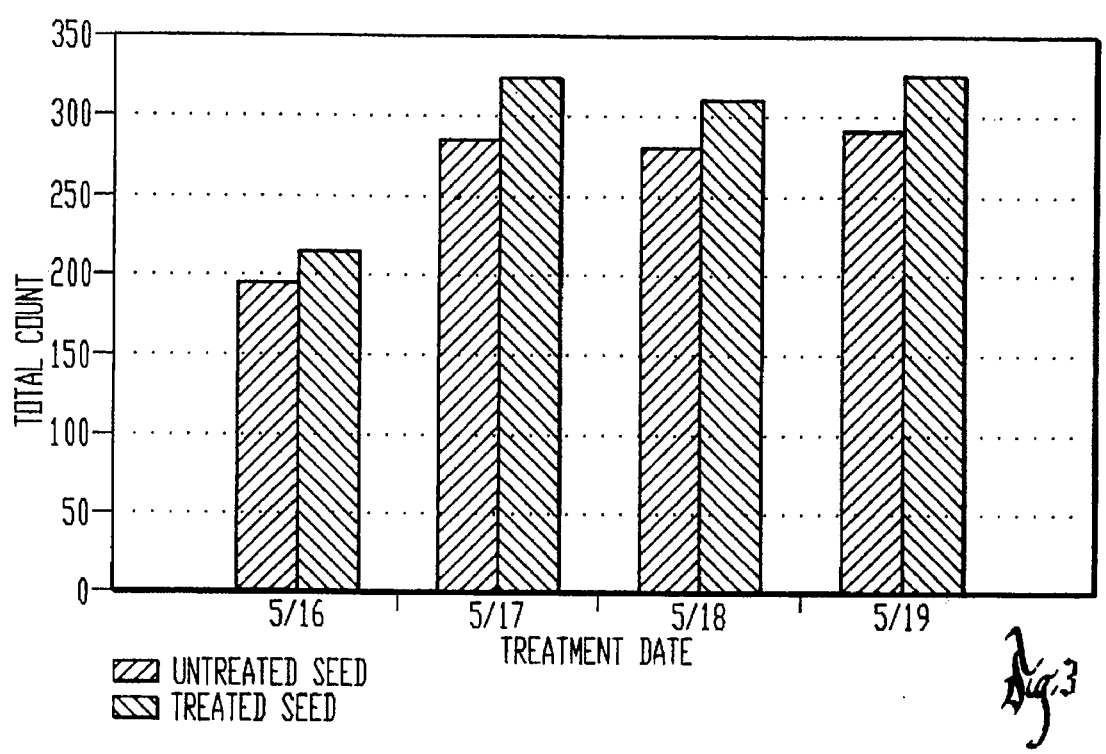
FIG. 3 shows Dixon, Ill., corn trials for the seed treatment of this invention as illustrated in Table 3 for trial 1.

Field trials were conducted in Dixon, Ill. with the sodium polyaspartate applied to corn seed in exactly the same manner as illustrated in Example 1. Table 3 shows the results of these Dixon, Ill. field trials, and trial 1, at 1X fertilizer treatment is graphically illustrated in FIG. 3.

TABLE 3

Dixon, IL - Corn Emergence From Seed (Total Count)

| Trial Sets | | Fertilizer Rates | | |
|---|---|---|---|---|
| | | 1× | ½× | ¼× |
| 1st Set | Treated | 212 | 198 | 185 |
| | Control | 193 | 203 | 178 |
| 2nd Set | Treated | 322 | 198 | 291 |
| | Control | 283 | 203 | 275 |

In all the above examples it can be seen that time to germination was shortened, time to emergence was shortened, and there was increased survivability of the seedling as it emerged, as indicated by the stand counts.

It can therefore be seen that the invention accomplishes at least all of its stated objectives.

What is claimed is:

1. A method of enhancing seedling development, said method comprising:
applying to seeds of agricultural crops, a small but seedling development treatment effective amount of a water-soluble, non-aromatic polyorganic acid or salts thereof which is a polyamino acid of the group consisting of polyaspartic acid, polyglutamic acid, polyglycine, polylysine, a copolymer of cysteine, glutamic acid and aspartic acid, said polyamino acid having a molecular weight larger than 1,500, wherein the water soluble non-aromatic polyamino acid is applied to the seeds in combination with other seed treating agents.

2. The method of claim 1 wherein the polyamino acid is polyaspartic acid.

3. The method of claim 1 wherein the polyamino acid salts are sodium, potassium or ammonium salts.

4. The method of claim 1 wherein the polyamino acid salt is sodium salt.

5. The method in accordance with claim 1 wherein the polyamino acid is polyaspartic acid having a molecular weight in the range of about 1,500 to about 40,000.

6. The method in accordance with claim 1 wherein the polyamino acid is polyaspartic acid having a molecular weight in the range of about 3,000 to about 5,000.

7. The method of claim 1 wherein the seeds are monocotyledons.

8. The method of claim 5 wherein the seeds are corn seeds.

9. The method of claim 1 wherein the seeds are wheat.

10. The method of claim 1 wherein the seeds are dicotyledons.

11. The method of claim 8 wherein the seeds are soybean seeds.

12. The method of claim 10 wherein the other seed treating agents are selected from the group consisting of insecticides, seed nutrients, and seed and seedling disease treatments.

13. The method of claim 1 wherein the water-soluble polyamino acid is applied in combination with a seedling acceptable carrier.

14. The method of claim 13 wherein the carrier is a liquid carrier.

15. The method of claim 13 wherein the carrier is a solid carrier.

* * * * *